United States Patent [19]

Roblin, III et al.

[11] Patent Number: 5,693,467
[45] Date of Patent: Dec. 2, 1997

[54] MYCOPLASMA POLYMERASE CHAIN REACTION TESTING SYSTEM USING A SET OF MIXED AND SINGLE SEQUENCE PRIMERS

[75] Inventors: Richard O. Roblin, III; Mendong Hu; Jane S. Tang; Sunmin Lee, all of Rockville, Md.

[73] Assignee: The American Type Culture Collection, Rockville, Md.

[21] Appl. No.: 445,289

[22] Filed: May 19, 1995

[51] Int. Cl.$^6$ .............. C12Q 1/68; C12P 19/34; C07H 21/04; C07H 21/02
[52] U.S. Cl. .............. 435/6; 435/91.2; 536/24.3; 536/24.32; 536/23.1
[58] Field of Search ......... 435/6, 91.2; 536/24.3–24.32, 536/23.1

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,965,188 | 10/1990 | Mullis et al. | 435/6 |
| 5,340,728 | 8/1994 | Grosz et al. | 435/91.2 |
| 5,427,909 | 6/1995 | Okamoto et al. | 435/54 |

FOREIGN PATENT DOCUMENTS

| | | | |
|---|---|---|---|
| 0475185A | 3/1992 | European Pat. Off. | C12N 15/31 |
| 0576743A | 1/1994 | European Pat. Off. | C12Q 1/68 |
| 3161000 | 2/1991 | Japan | C12Q 1/68 |
| 3254700 | 4/1991 | Japan | C12Q 1/68 |
| 4004899 | 1/1992 | Japan | C12Q 1/68 |
| 4173100 | 3/1992 | Japan | C12Q 1/68 |
| WO9205280 | 4/1992 | WIPO | C12Q 1/68 |
| WO9207095 | 4/1992 | WIPO | C12Q 1/68 |

OTHER PUBLICATIONS

R. Harasawa et al., Rapid Diagnosis of Mycoplasmas, [eds. Kahane & Adoni (New York)] pp. 227–232 (1993).

G. Rawadi et al., PCR Methods & Applications, (Long Island, New York) 4:199–208 (1995).

F.J.M. Van Kuppeveld et al., Appl. Env. Microbiol., 60:149–152 (1994).

J.G. Mattson et al., FEMS Microbiol. Lett. (Amsterdam, The Netherlands) 107:139–144 (1993).

T. Uemori et al., System. Appl. Microbiol. (Stuttgart, Germany) 15:181–186 (1992).

H. Kirchhoff et al., Biochemica (Oulu, Finland) 1:33–35 (1995).

R. Harasawa, Mol. & Diag. Proced. in Mycoplasmology, vol. IIA4 [eds. Razin & Tully (New York)] (1995).

G.J. McGarrity et al., Mycoplasmas. Mol. Biol. & Path. [eds. J. Maniloff et al.,(Wash. DC)] pp.445–454 (1992).

R. Harasawa et al., Res. Microbiol. (Paris, France) 144:489–493 (1993).

S. Deng et al., J. of Microbiol. Methods (Amsterdam, The Netherlands) 14:53–61 (1991).

Boehringer Mannehim 1995 Biochemicals Catalog (Indianopolis, IN) p. 171 (1995).

Takara Shuzo Co. Ltd., PCR Mycoplasma Detection Set Manual (USA).

Takara Shuzo Inc J04004899 09 Jan. 1992, Cited as Genbank Sequence Listing.

*Primary Examiner*—W. Gary Jones
*Assistant Examiner*—Dianne Rees
*Attorney, Agent, or Firm*—Whitham, Curtis, Whitham & McGinn

[57] ABSTRACT

The present invention relates to an enhanced system for specific, sensitive and rapid detection of the presence and identification of the specific mycoplasma contained in a sample of nucleic acid, wherein the sample nucleic acid is amplified using nested PCR which uses a mixture of first stage and second stage primers, each comprising at least one single sequence and at least one mixed sequence primer.

18 Claims, 3 Drawing Sheets

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

ACACCATGGG AGCTGGTAAT         20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:2:

ACACCATGGG AGTTGGTAAT         20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:3:

CTCCTAGTGC CAAGCCATCC         20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:4:

CTCCTAGTGC CAAGGCATCC         20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:5:

CTCCTAGTGC CAAGCCATTC         20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CTCCTAGTGC CAAGGCATTC                                              20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:7:

GTGCGGATGG ATCACCTCCT                                              20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:8:

GTGGGGATGG ATCACCTCCT                                              20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:9:

GTGCGGCTGG ATCACCTCCT                                              20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:10:

GTGGGGCTGG ATCACCTCCT                                              20

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:11:

GCATCCACCA AAAACCCTT                                               19

( 2 ) INFORMATION FOR SEQ ID NO:12:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear (xi) SEQUENCE DESCRIPTION: SEQ ID NO:12:

GCATCCACCA TAAACCCTT                                                                                          19

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear     (xi) SEQUENCE DESCRIPTION: SEQ ID NO:13:

GCATCCACCA AATACCCTT                                                                                          19

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear     (xi) SEQUENCE DESCRIPTION: SEQ ID NO:14:

GCATCCACCA TATACCCTT                                                                                          19

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear     (xi) SEQUENCE DESCRIPTION: SEQ ID NO:15:

GCATCCACCA AAAACTCTT                                                                                          19

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear     (xi) SEQUENCE DESCRIPTION: SEQ ID NO:16:

GCATCCACCA AATACTCTT                                                                                          19

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear     (xi) SEQUENCE DESCRIPTION: SEQ ID NO:17:

GCATCCACCA TAAACTCTT                                                                                          19

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear     (xi) SEQUENCE DESCRIPTION: SEQ ID NO:18:

GCATCCACCA TATACTCTT                                                                19

( 2 ) INFORMATION FOR SEQ ID NO:19:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

CTTCATCGAC TTCCAGACCC AAGGCAT                                                       27

( 2 ) INFORMATION FOR SEQ ID NO:20:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

CTTCTTCGAC TTCCAGACCC AAGGCAT                                                       27

( 2 ) INFORMATION FOR SEQ ID NO:21:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

CTTCATCGAC TTTCAGACCC AAGGCAT                                                       27

( 2 ) INFORMATION FOR SEQ ID NO:22:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

CTTCTTCGAC TTTCAGACCC AAGGCAT                                                       27

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

AAAGTGGGCA ATACCCAACG C                                                             21

( 2 ) INFORMATION FOR SEQ ID NO:24:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

TCACGCTTAG ATGCTTTCAG CG                                                            22

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:25:

CCACTGTGTG CCCTTTGTTC CT          22

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:26:

TATATTGGTG GAGCCTAGCG G          21

( 2 ) INFORMATION FOR SEQ ID NO:27:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:27:

ATTGGTGGAG CCTAGCGG          18

MYCOPLASMA POLYMERASE CHAIN REACTION TESTING SYSTEM USING A SET OF MIXED AND SINGLE SEQUENCE PRIMERS

FIELD OF THE INVENTION

This invention relates to a mycoplasma detection system using a "nested" (two-stage) polymerase chain reaction (PCR) that uses a mixture of "mixed sequence" and "single sequence" oligonucleotide primers. In the first PCR reaction, a mixture of "outer" or first stage primers is used to amplify a specific region of the mycoplasma DNA. The amplicons from this first reaction serve as the template for a second reaction, wherein the amplicons are further amplified in the second reaction using a mixture of "inner" or second stage primers. This system accurately and consistently detects a number of commonly encountered mycoplasma contaminants in cell cultures, viral stocks and biopharmaceutical reagents, including the contaminant often undetected *Acholeplasma laidlawii*, and further detects Mycoplasma-Like Organisms (MLO). The system is very sensitive and very specific, showing almost no cross-reaction with related bacteria and mammalian cells.

BACKGROUND OF THE INVENTION

Mycoplasma are prokaryotic microorganisms belonging to the class Mollicutes. About 100 mycoplasma species are currently known and they are classified into six genera. Mycoplasma lack a cell wall and are almost always found in close contact with eukaryotic cells. Many mycoplasma are pathogens.

A wide variety of cell cultures can be contaminated with mycoplasma, posing a problem for many scientists. In addition, virus stocks, live virus vaccines and biopharmaceutical drugs that are prepared using animal cell cultures may become contaminated with mycoplasma.

Mycoplasma are prevalent in continuously growing cell lines. The contamination by mycoplasma has been a serious problem, and adversely affects experimental research. Studies have shown that cell cultures are frequently infected up to 5–87% with mycoplasma. [Rawadi and Dussurget, "Advances in PCR-based Detection of Mycoplasmas Contaminating Cell Cultures", PCR Methods and Applications, 4, pp. 199–208 (1995)]. In addition, in some cases it is difficult to eliminate mycoplasmas from contaminated cell cultures.

Contamination by mycoplasma cannot be detected by viewing cultures. In addition, mycoplasma are not always detectable with macroscopic alteration of the cells or media. Many mycoplasma contaminants grow slowly and do not destroy the host cells. However, adverse effects of mycoplasma contamination, such as changes in metabolism, growth, viability, DNA, RNA and protein synthesis, pH shift, and morphology, etc., are still numerous. Another problem associated with mycoplasma contamination is that most cytokine-producing cell lines are not only contaminated with mycoplasmas, but are also induced by the mycoplasmas. Thus, mycoplasma contamination in cell cultures may lead to unreliable experiments and mycoplasma contaminated biological products.

Therefore, it is important to test for mycoplasma contamination of cell cultures. It is also useful to identify the species of mycoplasma contaminants as an indication of possible sources of the mycoplasma. To date, several techniques have been used to detect mycoplasma contamination of cell cultures. These include culture procedures on agar, broth, or semi-solid agar-broth medium; propagation on susceptible indicator cell lines for detection of mycoplasma species that are not cultivable in cell-free medium; DNA-staining procedures with dyes like DAPI (4',6-diamine 2'-phenylindole dihydrochloride) or H 33258 (bisbenzimide); biochemical identification methods that detect enzyme activities present in mycoplasmas but absent or minimal in non-infected cell cultures; DNA-hybridization procedures, mostly based on mycoplasmal ribosomal RNA genes; detection by specific fluorescein- or peroxidase-conjugated polyclonal antisera or monoclonal antibodies with fluorescence microscopy, enzyme-linked immunosorbent assays (ELISA, as in the Boehringer Mannheim Mycoplasma Detection Kit); and use of the polymerase chain reaction (PCR), which recently has been applied for the detection of mycoplasmas in cell cultures (Rawadi, et. al. at 199–206). The polymerase chain reaction has proven more successful as compared to earlier methods which lack combined sensitivity, specificity and speed.

The PCR process for amplifying and detecting nucleic acid sequences is described in U.S. Pat. Nos. 4,683,202; 4,683,195; and 4,965,188, which are hereby incorporated by reference. The basic purpose of PCR is to amplify DNA. The PCR process consists of the following three steps which are repeated in cyclic fashion so that the primer extension products of each cycle become the templates for replication in subsequent cycles: 1) denaturation of the template at elevated temperature; 2) annealing at hybridization temperature of oligonucleotide primers to the single-stranded template DNA; and 3) extension by a thermostable DNA polymerase in the presence of nucleotide triphosphates of the 3' ends of the primers in order to replicate the desired template sequence. Repetition of this process results in the formation of DNA strands that correspond in sequence to the region between the originally used primers. Specific PCR primer pairs are used to identify particular mycoplasma species.

PCT WO 92/07095 discloses use of an arbitrarily primed polymerase chain reaction (AP-PCR), in order to detect bacterial species and strains, including Staphylococcus and Streptococcus species. The process involves use of arbitrary primers used at low stringency hybridization conditions in order to generate specific discrete products that can be resolved into a small number of individual bands providing a species "fingerprint." Specifically, the method consists of the following steps: 1) priming target nucleic acid of a genome with a single-stranded primer to form primed nucleic acid such that a substantial degree of internal-mismatching occurs between the primer and the target nucleic acid; 2) amplifying the primed nucleic acid by performing at least one cycle of PCR amplification; and 3) amplifying the product of step (2) by performing at least about 10 cycles of PCR amplification.

However, there are limitations to the use of PCR alone in mycoplasma testing. For example, enhanced sensitivity and/or specificity is desirable.

Nested PCR has been shown to increase the sensitivity of the mycoplasma test by at least two orders of magnitude while minimizing background from non-target DNA amplification. [Garson et al., *Lancet*, p. 335, 1419 (1990); Proter-Jordan, et al., *J. Med. Virol.*, p. 30, 85 (1990); Harasawa et al., "Rapid Diagnosis of Mycoplasmas," (Kahane I. and Adoni A. eds.) p. 227–231 (1993)].

The process of nested PCR refers to a two stage PCR reaction in which in the first stage 1) a pair of outer primers which flank a particular DNA segment are used to amplify that first DNA segment in stage 1, followed by a second stage 2) in which a second set of inner primers is used to amplify a smaller "target" segment of nucleic acid which is contained within the first DNA segment. The nested PCR is currently the most sensitive means for detecting mycoplasma in cell cultures for the reason that a single copy of the target DNA can be detected.

U.S. Pat. No. 5,340,728 relates to a kinetically controlled nested PCR amplification method used to assay for microbial contaminants in food. The basic concept involves controlling the concentrations of the outer and inner nested primers and annealing times in the first and second stages, which results in highly specific and efficient amplification of a targeted piece of DNA. For effective nested PCR amplification, the amplification of the outer primer set must be terminated after the first stage to allow the inner primers to amplify the DNA in the second stage.

Mattsson et al, "Oligonucleotide Probes Complementary to 16S rRNA for Rapid Detection of Mycoplasma Contamination in Cell Cultures," *FEMS Microbiology Letters* 107, 139–144 (1993), disclose a method for detecting mycoplasma contamination using three different oligonucleotide probes complementary to 16S rRNA. Two of the probes were designed to be group-specific and one to be species-specific. Although the assay is rapid, allowing the possibility to perform and evaluate the mycoplasma testing within one working day, the method is not very sensitive.

Harasawa et al., "Detection and Tentative Identification of Dominant Mycoplasma Species in Cell Cultures by Restriction Analysis of the 16S–23S rRNA Intergenic Spacer Regions," *Res. Microbiol.*, 144, 489–493 (1993), teaches use of mixed sequence primers [5'(ACACCATGGGAG(C/T) TGGTAAT)3' (F1) (SEQ ID NO'S: 1–2)], [5' (CTCCTAGTGCCAAG(C/G)CAT(C/T)C)3' (SEQ ID NO'S: 3–6)] for use as first stage primers, and [5'(GTG(C/G)GG(A/C)TGGATCACCTCCT)3' (F2) (SEQ ID NO'S: 7–10)] and [5'(GCATCCACCA(A/T)A(A/T)AC(C/T)CTT) 3' (R2) (SEQ ID NO'S: 11–18)] for use as second stage primers. In addition, Harasawa [Harasawa, R. in: Molecular and Diagnostic Procedures in Mycoplasmology (Razin, S. and J. E. Tully, eds.) Vol. IIA4 (i.v.) Academic Press, in press (1995)] teaches use of the mixed sequence primer [5'(CTTC (A/T)TCGACTT(C/T)CAGACCCAAGGCAT)3' (SEQ ID NO'S: 19–22)] in place of [5'(CTCCTAGTGCOAAG(C/G) CAT(C/T)C)3' (SEQ ID NO'S: 3–6)]. However, a relatively large amount of *A. laidlawii*, (i.e., about $10^3$–$10^4$ CFU/ml) must be present in the sample in order for the test to accurately detect this mycoplasma species. Further, there is a likelihood of cross-reactivity occurring between human and mycoplasma species by use of the Harasawa method.

It is a requirement that researchers perform routine assays for possible contamination of all cell cultures. However, current mycoplasma testing methods are not highly sensitive and specific. *Mycoplasma fermentans*, *M. hyorhinis* (porcine origin), *M. orale* (human origin), *M. arginini*, and *Acholeplasma laidlawii* (bovine origin), account for more than 95% of the mycoplasma contamination in cell cultures [McGarrity et al., "Mycoplasmas and Tissue Culture Cells" in Mycoplasmas. Molecular Biology and Pathogenesis. (ed. J. Maniloff, et al.) pp. 445–454 American Society for Microbiology, Washington, D.C. (1992)]. *M. pirum*, *M. hominis*, and *M. salivarium* are also common contaminants of cell culture. However, most known mycoplasma test kits do not detect all eight Mycoplasma species.

Further, most detection systems are not sensitive and specific enough to detect and identify *A. laidlawii*, because the primers are designed for detection of Mycoplasma. Since Mycoplasma and Acholeplasma are two different genera, the primers that detect Mycoplasma may not necessarily detect Acholeplasma. Therefore, most mycoplasma detection systems detect either Acholeplasma or Mycoplasma, but not both.

There exists a need for a single highly specific, highly sensitive, and rapid system for detecting and identifying a variety of known mycoplasma species and MLO, including *A. laidlawii*.

SUMMARY OF THE INVENTION

The present invention provides a highly specific, highly sensitive, rapid system for detecting and identifying a variety of known mycoplasma species and MLO, including *A. laidlawii*, *M. fermentans*, *M. hyorhinis*, *M. orale*, *M. arginini*, *M. pirum*, *M. hominis*, and *M. salivarium*. The system involves use of nested PCR, a two-stage amplification method, to produce different sized DNA amplicons depending upon the Mycoplasma or Acholeplasma species. The invention is characterized in that mixtures of single sequence and mixed sequence oligonucleotides are used as the "outer" and "inner" primers. The combination of nested PCR, along with a mixture of single sequence and mixed sequence oligonucleotide primers complementary to the DNA sequence of the aforementioned Mycoplasmas and *A. laidlawii*, provides enhanced specificity and sensitivity.

The present invention includes a method for amplifying a target segment of nucleic acid in a nucleic acid mixture by performing a nested polymerase chain reaction to selectively amplify a target segment of nucleic acid from said sample nucleic acid reaction mixture, wherein said method comprises the steps of: a) adding a first stage primer mixture to a sample nucleic acid reaction mixture, wherein said first stage primer mixture contains a mixture of at least one single sequence and at least one mixed sequence oligonucleotide primers, in order to amplify a nucleic acid segment flanked by said outer primer pair; b) repetitively performing the polymerase chain reaction; c) adding a second stage primer mixture to said nucleic acid reaction mixture, wherein said second stage primer mixture contains a mixture of at least one single sequence and at least one mixed sequence oligonucleotide primers, in order to selectively amplify a target nucleic acid segment flanked by said inner primers; and d) repetitively performing the polymerase chain reaction.

The present invention further comprises a mycoplasma test kit for detection of the presence of a selectively amplified target segment of a nucleic acid in a nucleic acid mixture, comprising: a) a first stage primer mixture as described above; b) a second stage primer mixture as described above; c) a first positive control nucleic acid 1; and d) a second positive control nucleic acid 2.

DETAILED DESCRIPTION OF THE DRAWINGS

DETAILED DESCRIPTION OF THE INVENTION

Mixed sequence primers are used in PCR reactions to obtain consistent amplification of similar target DNA sequences, for example, those from closely related microorganisms. When it is desired to extend the breadth of detection of the PCR amplification, without losing the detection of the closely related microorganisms, single sequence primers can be combined with the mixed sequence primers to accomplish this objective.

Applications of this concept include simultaneous PCR testing for multiple, specific infectious agents, each of which can cause the observed, or similar symptoms. In a preferred embodiment, this concept is applied to consistent and sensitive detection of the members of a group of infectious agent (class Mollicutes) that can cause "mycoplasma contamination" of cell cultures.

As is evident to those skilled in the art, oligonucleotide primers of defined sequence, including "mixed sequence" primers, can be prepared by chemical synthesis, now performed by several commercial organizations. These chemical syntheses are well known to one of ordinary skill in the relevant art.

The present invention uses two distinguishable types of oligonucleotide primers. Primers such as [5' (ACACCATGGGAG(C/T)TGGTAAT)3' (SEQ ID NO'S: 1-2)] are chemically synthesized using equal molar amounts of C and T at position 13, are assumed to contain equal molar amounts of the oligonucleotides 5'(ACACCATGGGAGCTGGTAAT)3' (SEQ ID NO: 1) and 5'(ACACCATGGGAGTTGGTAAT)3' (SEQ ID NO: 2), and are designated "mixed sequence" primers. Primers such as

[5'(AAAGTGGGCAATACCCAACGC)3' (SEQ ID NO: 6)]

are designated "single sequence" primers.

The first stage primer mixture and the second stage primer mixture comprise multiple oligonucleotide primers, wherein these primers comprise at least one single sequence primer and at least one mixed sequence primer. Preferably, at least one of the primers is specifically complementary to *A. laidlawii* DNA, in order to amplify a Mycoplasma- and/or Acholeplasma-specific nucleic acid segment.

Specific "mixed sequence" primers and "single sequence" primers can be combined to yield the "first stage primer mixture" and "second stage primer mixture." Examples of preferred primers useful in the present invention are summarized in Table 1.

TABLE 1

Examples of oligonucleotide primer mixtures suitable for use in the mycoplasma detection kit.

| Primer Sequence (All sequences written 5' to 3') | Primer Sequence Name(s) |
|---|---|
| First Stage Primer Mixture | |
| ACACCATGGGAG (C/T) TGGTAAT, SEQ ID NO'S: 1-2 | F1, MCGpF11 |
| CTTC (A/T) TCGACTT (C/T) CAGACCCAAGGCAT, SEQ ID NO'S 19-22 | R1 |
| AAAGTGGGCAATACCCAACGC, SEQ ID NO: 23 | M78 |
| TCACGCTTAGATGCTTTCAGCG SEQ ID NO: 24 | M89 |

TABLE 1-continued

Examples of oligonucleotide primer mixtures suitable for use in the mycoplasma detection kit.

| Primer Sequence (All sequences written 5' to 3') | Primer Sequence Name(s) |
|---|---|
| Second Stage Primer Mixture | |
| GTG (C/G) GG (A/C) TGGATCACCTCCT, SEQ ID NO'S: 7-10 | R16-2, F2 |
| GCATCCACCA (A/T) A (A/T) AC (C/T) CTT, SEQ ID NO'S: 11-18 | MCGpR21, R2 |
| CCACTGTGTGCCCTTTGTTCCT, SEQ ID NO: 25 | M34 |

Of the outer primers listed above, F1 [i.e., 5'(ACACCATGGGAG(C/T)TGGTAAT)3' (SEQ ID NO'S: 1-2)] is present in the form of an equal molar amount of 5'(ACACCATGGGAGCTGGTAAT)3' (SEQ ID NO: 1), and 5'(ACACCATGGGAGTTGGTAAT)3' (SEQ ID NO: 2). Similarly, R1 [i.e., 5'(CTTC(A/T)TCGACTT(C/T)CAGACCCAAGGCAT)3' (SEQ ID NO'S: 19-22)] is present in equal molar amounts of 5'(CTTCATCGACTTCCAGACCCAAGGCAT)3' (SEQ ID NO: 19), 5'(CTTCATCGACTTTCAGACCCAAGGCAT)3' (SEQ ID NO: 21), 5'(CTTCTTCGACTTCCAGACCCAAGGCAT)3' (SEQ ID NO: 20), and 5'(CTTCTTCGACTTTCAGACCCAAGGCAT)3' (SEQ ID NO: 22).

Of the inner primers listed above, F2 [i.e., 5'(GTG(C/G)GG(A/C)TGGATCACCTCCT)3' (SEQ ID NO'S: 7-10)] is present in equal molar amounts of 5'(GTGCGGATGGATCACCTCCT)3' (SEQ ID NO: 7), 5'(GTGGGGCTGGATCACCTCCT)3' (SEQ ID NO: 10), 5'(GTGCGGCTGGATCACCTCCT)3' (SEQ ID NO: 9) and 5'(GTGGGGATGGATCACCTCCT)3' (SEQ ID NO: 8). Similarly, R2, [i.e., 5'(GCATCCACCA(A/T)A(A/T)AC(C/T)CTT)3' (SEQ ID NO'S: 11-18)] is present in equal molar amounts of 5'(GCATCCACCAAAAACCCTT)3' (SEQ ID NO: 1), 5'(GCATCCACCAAAAACTCTT)3' (SEQ ID NO: 15), 5'(GCATCCACCAAATACCCTT)3' (SEQ ID NO: 13), 5'(GCATCCACCAAATACTCTT)3' (SEQ ID NO: 16), 5'(GCATCCACCATAAACCCTT)3' (SEQ ID NO: 12), 5'(GCATCCACCATAAACTCTT)3' (SEQ ID NO: 17), 5'(GCATCCACCATATACCCTT)3' (SEQ ID NO: 14), and 5'(GCATCCACCATATACTCTT)3' (SEQ ID NO: 18).

The outer and inner primers can be present in an amount of from 10–40 pmol/μl, preferably 20 pmol/μl.

Although the above listed primers comprise the preferred method of the invention, the invention is not intended to be limited to these primers and can be used with any suitable primer set, comprising at least one single sequence and at least one mixed sequence primer.

The present invention involves use of a "nested" PCR reaction, which refers to a two-stage amplification reaction in which in stage 1) a segment of nucleic acid is amplified using a first stage primer mixture comprised of both mixed sequence primers and single sequence primers, followed by a second stage 2) in which a second stage primer mixture comprised of both mixed sequence primers and single sequence primers is used to further amplify a smaller segment of target nucleic acid. Both first- and second-stage primers will flank the target nucleic acid. As a result, the final amplified product is obtained within the frame of the first segment of nucleic acid.

Prior to addition of the primer mixtures, nucleic acid can be extracted and precipitated. This is usually not necessary in PCR assays for detection of mycoplasmas in fresh cell cultures or in fetal calf serum. However, it is recommended that nucleic acid be extracted from test samples which may contain inhibitors of PCR, i.e., samples directly taken from frozen cell cultures or from reconstituted, lyophilized virus stocks and other biological material.

The present method includes partial purification of nucleic acid from the test samples which can be done by a number of means. (Refer to: "THE POLYMERASE CHAIN REACTION" (MULLIS K. B., FERRE F., and GIBBS R. A. eds.) (1994) Birkhauser Boston, p.48–49). For example, the mycoplasma cells can be concentrated followed by cell-lysis, then the released nucleic acid is precipitated and further dissolved for PCR.

After the sample is prepared, the first-stage primer mixture and other necessary reagents are added and followed by the PCR. An aliquot of the resulting reaction mixture is then added to the second-stage reaction mixture with second-stage primer mixture and again subjected to nested PCR. The PCR reaction and nested PCR method are both disclosed in U.S. Pat. No. 4,683,202, which is hereby incorporated by reference. Although the present invention uses two stages of amplification, the present invention can be modified to use more than two stages of amplification. Specifically, three or even more stages of amplification can be employed, especially if additional selectivity in the amplification of target nucleic acid is desired.

Figure 1:
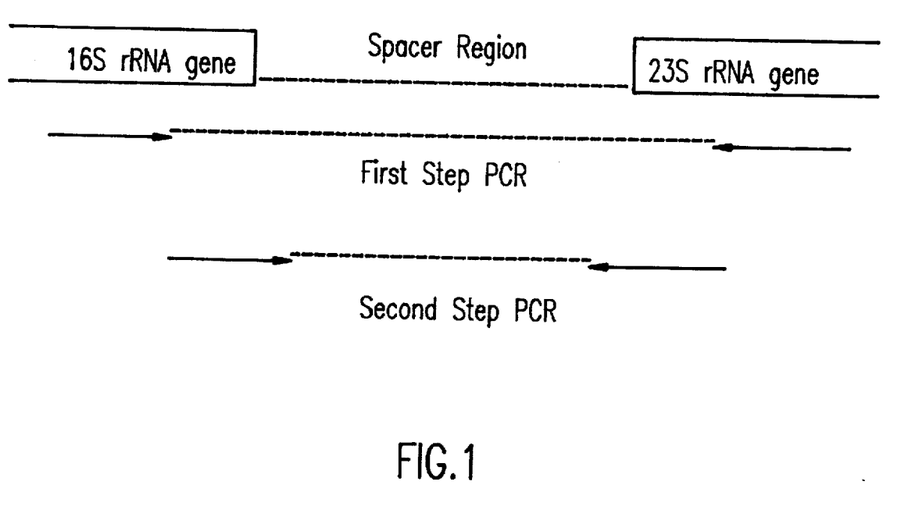
FIG. 1 shows a strategy for two-step PCR.

An outline of the strategy for the two-step PCR as used in the present invention is shown in FIG. 1.

PCR can be carried out in any authorized thermal cycler, particularly according to instructions in a Perkin-Elmer Model 2400 thermal cycler. A preferred temperature profile for this PCR reaction is first to denature the nucleic acid at 94° C. for 30 seconds, then perform 30 cycles each of which consists of denaturation at 94° C. for 30 seconds, annealing primers at 55° C. for 2 minutes, and extension at 72° C. for 2 minutes. Afterwards, it is preferred that the cycler be heated an additional 5 minutes at 72° C. Optimization of the denaturation-hybridization-synthesis conditions for alternative oligonucleotides is well within the skill in the art.

The present invention uses PCR to amplify the spacer region between 16S and 23S rRNA genes of mycoplasmas. Preferred primer sequences useful in the present invention are derived from conserved regions of Mycoplasma rRNA operons. In general, any suitable primer which is complementary to the conserved DNA region of a Mycoplasma species can be used in the present invention. However, the present invention is not intended to be limited to these primers.

Specifically referring to the hard to detect species, A. laidlawii, this species has at least two rRNA operons, each having different sequences in the spacer region. In a preferred embodiment of the invention, the A. laidlawii-specific primers M78, M89 and M34 are used in order to consistently produce a two-banded PCR product from A. laidlawii genomic DNA. This is in contrast to other mycoplasma test kits which do not consistently produce a two-banded PCR product for the detection of A. laidlawii.

Identification of Mycoplasma and Acholeplasma contaminants can be done using size identification techniques or using known restriction enzyme digest mapping in order to identify the specific mycoplasma species present in a sample. For example, the size of each second stage PCR amplicon can be estimated by resolving the product in 3–4% Nusieve 3:1 agarose (FMC), 1.2% agarose (Gibco BRL), 2 to 3% metaphor agarose (FMC), or using 5% polyacrylamide gel followed by ethidium bromide staining. Any matrix that is suitable for distinguishing nucleic acids of the size of the expected PCR products can be used.

Also, restriction enzyme digestion can be used for identification of diagnostic fragments. For example, restriction endonucleases (VspI, ClaI, HindIII, HaeIII) can be used to digest the second stage products from the commonly encountered mycoplasma. Digested PCR products can be resolved by electrophoresis on 5% polyacrylamide gel or 2–3% metaphor agarose (FMC) with ethidium bromide staining.

Usually, the second stage PCR product is used for determination. It is recommended to use 1.2% agarose (BRL) for the resolution of the amplified DNA products.

Using primer mixtures in the present invention, Mycoplasma contaminants should generate a one-banded product in the range of 236–365 bp. In addition, A. laidlawii should consistently produce a double-banded product. Positive and negative controls should be included to ensure that the PCR conditions are correct and the reaction is working. Suitable positive controls for a mycoplasma assay are, for example, M. pirum DNA and A. laidlawii DNA. M. pirum DNA control template should produce a single band of 323 bp. A double-banded product (426 bp and 219 bp, respectively) would be seen for A. laidlawii after the second run PCR. The negative control can be distilled water in the place of the template. No discrete band should be seen after the second stage PCR in this case.

Any other suitable identification technique can be used to identify the amplified nucleic acid resulting from the present method. For example, suitable identification techniques include digestion with specific restriction enzymes, and nucleic acid hybridization with Mycoplasma species-specific probes.

The present invention further includes a mycoplasma test kit for detection of the presence of a selectively amplified target segment of a nucleic acid in a nucleic acid mixture. The kit comprises: 1) a first stage primer mixture containing a mixture of at least one single sequence and at least one mixed sequence oligonucleotide primers; 2) a second stage primer mixture, wherein said second stage primer mixture contains a mixture of at least one single sequence and at least one mixed sequence oligonucleotide primers; 3) a first positive control nucleic acid 1; and d) a second positive control nucleic acid 2. For example, the preferred primers and amounts listed above apply to the kit as well. Moreover, the reagents can be provided in a more concentrated form for dilution to the appropriate concentrations and amounts by the end user.

Also present in the kit are one or more positive nucleic acid controls as listed above. Other Mycoplasma genomic DNA can be used as the positive controls. For example, genomic DNA of ATCC 17981, M. hyorhinis; ATCC 19989, M. fermentans; ATCC 23064, M. salivarium; ATCC 23114, M. hominis; ATCC 23714, M. orale; and ATCC 23838, M. arginini can be included in the kit.

The positive control nucleic acids can be present in the kit in an amount of from 5 ng to 50 ng, preferably 10 ng in 50 μl of solution, preferably sterile, distilled water. Other suitable buffers that do not inhibit the PCR reaction can be used. The first stage and second stage primer mixtures are present in the kit in an amount of 0.5 to 5 nmoles, preferably 1 nmole in 50 μl of solution, preferably sterile, distilled water. The first stage and second stage primer mixtures of the kit can be provided in an amount to enable a plurality of tests, such as, for at least 50 reactions. Similarly, the two positive controls of the kit can be used for at least 10 reactions. It is desirable for a kit of the present invention to be stored at −20° C. In the case of the exemplified mycoplasma kit, components of the kit are stable upon freezing and thawing for up to 12 times.

The kit of the present invention can comprise a plurality of vessels housing the components of the kit. For example, one or more separate vessels can contain a first stage primer set, a second stage primer set, a first positive control and a second positive control, all of which have been previously identified.

Preferably the kit of the present invention will comprise a plurality of vessels, wherein a first vessel contains a mixture of first stage predetermined primers mixture comprising at least one single sequence and at least one mixed sequence oligonucleotide; a second vessel containing a mixture of second stage predetermined primers, wherein said second stage predetermined primers mixture comprises at least one single sequence oligonucleotide and a least one mixed sequence oligonucleotide; a third vessel containing a first positive control nucleic acid; and a fourth vessel containing a second positive control nucleic acid.

The vessels can be of any size suitable for housing the above components and suitable for safe and secure transport. The size of the vessels will depend on the amount of solution desired. For example, the vessels can be cylindrical, tubular, cubical, rectangular, or the like. Although any suitable material can be used for the composition of the vessels, it is preferred that the vessels are plastic or glass-like test tubes. The tubes can be packaged in any container capable of storing and transporting one or more vessels.

The present invention is useful for amplifying nucleic acids from environmental samples or research samples of cell cultures, viral stocks, and biopharmaceutical reagents. In addition, the present invention can be used for diagnosis of mycoplasma, including MLO, infection in plants, insects, animals and in clinical isolates. Moreover, the present invention can be used for diagnostic or forensic purposes. Typical examples of these types of biological sources includes human or animal samples containing blood, urine, tissue, semen, bacterial and hair.

The method and kit of the present invention can be used for both detection of the presence of mycoplasma and for identification of the specific mycoplasma contained in the reaction sample. By "sample nucleic acid mixture", Applicants refer to a sample containing nucleic acids and mixtures thereof from any strain, species, class or genera of organisms. Specifically, a preferred embodiment of the method and kit of the present invention are applicable to amplifying a segment of DNA of the genome in class Mollicutes. Other specific examples include a microorganism selected from the group consisting of *Acholeplasma laidlawii, A. modicum, A. morum, Mycoplasma fermentans, M. hyorhinis, M. orale, M. hominis, M. arginini, M. pirum, M. salivarium, M. hyopneumoniae, M. neurolyticum, M. pulmonis, M. pneumoniae, M. capricolum, M. arthritidis, M. gallinarum, M. hyosynoviae, M. mycoides, M. bovis, Entomoplasma ellychniae, Em. lucivorax, Em. melaleucae, Em. somnilux, Mesoplasma entomophilum, Ms. pleciae, Ms. photuris, Ms. chauliocola, Ms. corruscae, Ms. grammopterae, Ms. coleopterae, Ms. tabanidae, Ms. lactucae, Ms. seiffertii, Ms. florum, Ureaplasma urealyticum, U. gallorale, U. canigenitalium, U. diversum, Spiroplasma chinense, Sp. citri, Sp. floricola, Sp. kunkelii, Lactobacillus casei,* and *Lactobacillus rhamnosus.* No mycoplasma-specific amplicon bands were observed upon testing the following microorganisms: *Bacillus subtilis, L. catenaformis, Clostridium ramosum, C. innocuum, Escherichia coli, Enterococcus faecalis,* human DNA including ATCC CRL 1611, CCL 119, CCL 86, CCL 187, mouse DNA including ATCC HB 72, HB 96, HB 144, HB 167, HB 194, CRL 1581, rat DNA ATCC HB 219 and HB 221, hamster DNA HB 226 and HB 218, and monkey DNA ATCC CRL 1587, CCL 81. Therefore, the exemplified embodiment of the present invention is specific to mycoplasma organisms containing no cell wall, showing no cross-reactivity with many related bacteria (except for Lactobacillus), as well as mammalian cells.

The exemplified embodiment of the present invention is highly sensitive, possessing the ability to detect at least 0.1 to 1.6 colony-forming units (CFU) of Mycoplasma/Acholeplasma per sample (5 µl). The sensitivity for detecting *A. laidlawii* is as high as 0.1 CFU per 5 µl sample. This high sensitivity is particularly valuable when screening cell cultures contaminated with a low amount of mycoplasma, detecting those fastidious species of mycoplasma that hardly grow by the direct culture method, and in monitoring removal of mycoplasma contaminants from cell cultures by drug treatment.

The exemplified embodiment of the present invention also has a broad detection range, detecting a wide variety of Mycoplasma and Acholeplasma species and MLO's. The primer mixtures of the exemplified embodiment of the method and kit can universally detect all Mycoplasma and Acholeplasma species commonly encountered in cell cultures. The exemplified embodiment of the present invention also allows for rapid and easy use. The entire nested PCR assay can be completed within one working day. In addition, the results of the PCR assay are easy to read.

The instant invention now will be exemplified in the following non-limiting examples. Other embodiments of the present invention are not exemplified herein. However, it is not intended that Applicants be limited to the scope of the specific embodiments set forth herein.

EXAMPLES

Example 1

Extraction of DNA

DNA was extracted from test samples (listed in Table 6 below) possibly contaminated with mycoplasma and containing PCR inhibitors (i.e. samples directly taken from the frozen cell cultures or from reconstituted, lyophilized virus stocks).

An amount of 500 µl of cell suspension or reconstituted biological was transferred to a sterile microcentrifuge tube. The cells were collected by centrifugation at 12,000 g for 20 minutes in an Eppendorf microcentrifuge. The cell pellet was resuspended in 100 µl of lysis buffer (1× PCR buffer, 0.5% NP-40, 0.5% Tween 20). An mount of 1 µl proteinase K (17.3 mg/ml) was added to the suspension. The resulting suspension was incubated at 60° C. for one hour.

The enzyme was inactivated by heating at 95° C. for 10 minutes. An amount of 500 µl of $dH_2O$ was then added to the solution. Next, 600 µl isopropanol and 1 µl of glycogen (20 mg/ml) were added and the solution mixed gently by inverting the tube. The resulting solution was incubated at −20° C. for at least 30 minutes.

The DNA pellet was collected by centrifugation at 12,000 g for 30 minutes at 4° C. The supernatant was discarded and the DNA pellet washed in 500 µl of cold 75% ethanol. Next, the pellet was centrifuged at 12,000 g for 10 minutes at 4° C. The step of discarding the supernatant, washing the pellet, and centrifugation was repeated once again.

All the supernatant again was carefully discarded. The DNA pellet was allowed to dry. Next, the DNA was resuspended in 50 µl dH₂O and kept at 4° C., or -20° C. until ready for the nested PCR.

First Stage PCR

DNA was prepared as outlined above. In a 200 µl or a 500 µl tube, 36.8 µl sterile distilled water was mixed with 5 µl of 10× PCR buffer (100 mM Tris-HCl, pH 8.3; 500 mM KCl, 15 mM MgCl₂; and 0.01% w/v gelatin), 1 µl of dNTP's (2.5 mM each), 1 µl of 25 mM MgCl₂, 0.2 µl of 5 units/µl of Taq DNA polymerase. Next, 1 µl (20 pmole/µl each) of the "first stage primer mixture" was added. The first stage primer mixture sequences were as follows:

"Mixed sequence" primer F1
5'(ACACCATGGGAGCTGGTAAT)3' (SEQ ID NO: 1)
5'(ACACCATGGGAGTTGGTAAT)3' (SEQ ID NO: 2)
"Mixed sequence" primer R1
5'(CTTCATCGACTTCCAGACCCAAGGCAT)3' (SEQ ID NO: 19)
5'(CTTCTTCGACTTCCAGACCCAAGGCAT)3' (SEQ ID NO: 20)
5'(CTTCATCGACTTTCAGACCCAAGGCAT)3' (SEQ ID NO: 21)
5'(CTTCTTCGACTTTCAGACCCAAGGCAT)3' (SEQ ID NO: 22)
"Single sequence" primer M78
5'(AAAGTGGGCAATACCCAACGC)3' (SEQ ID NO: 23)
"Single sequence" primer M89
5'(TCACGCTTAGATGCTTTCAGCG)3' (SEQ ID NO: 24)

In a preferred embodiment, the relative molar ratios of the individual oligonucleotide components of F1, R1, M78 and M89 were 0.5:0.25:1:1, respectively. It will be evident to those skilled in the art that other molar ratios of the oligonucleotide primers, particularly ratios that increase the relative amount of the primers present in lowest concentration, may be advantageous.

Finally, 5 µl of the template DNA was added. The total reaction volume was 50 µl.

It is possible to make the reaction mixture in one stock and aliquot 45 µl of the mixture to each 200 µl or 500 µl tube, and then add 5 µl of template DNA or cell culture fluid.

For each PCR run, two positive DNA controls and one negative control should be included. For the positive control, 5 µl (1 ng) of M. pirum DNA and 5 µl (1 ng) of A. laidlawii DNA were pipetted into two separate tubes. For the negative control, 5 µl of sterile distilled water was pipetted into one tube.

The PCR reaction was carried out in a Perkin-Elmer thermal cycler for 30 cycles in order to amplify the DNA. The thermal cycler was first heated to 94° C. for 30 seconds, and then performed 30 cycles each consisting of 94° C. for another 30 seconds, 55° C. for 2 minutes, and 72° C. for 2 minutes. After the last of the 30 cycles, an additional 5 minutes at 72° C. was added.

Second Stage PCR

For the second stage reaction, in a 200 µl or a 500 µl tube, 40.8 µl of sterile distilled water was mixed with 5 µl of 10× PCR buffer (same as in the first stage PCR), 1 µl of dNTP's (2.5 mM each as in the first stage PCR), 1 µl of 25 mM MgCl₂, 0.2 µl of 5 units/µl of Taq DNA polymerase. Next, 1 µl (20 pmole/µl) of "second stage primer mixture" was added. The second stage primer mixture sequences were as follows:

"Mixed sequence" primer F2
5'(GTGGGGCTGGATCACCTCCT)3' (SEQ ID NO: 10)
5'(GTGGGGATGGATCACCTCCT)3' (SEQ ID NO: 8)
5'(GTGCGGATGGATCACCTCCT)3' (SEQ ID NO: 7)
5'(GTGCGGCTGGATCACCTCCT)3' (SEQ ID NO: 9)
"Mixed sequence" primer R2
5'(GCATCCACCAAAAACCCTT)3' (SEQ ID NO: 11)
5'(GCATCCACCATAAACCCTT)3' (SEQ ID NO: 12)
5'(GCATCCACCAAATACCCTT)3' (SEQ ID NO: 13)
5'(GCATCCACCATATACCCTT)3' (SEQ ID NO: 14)
5'(GCATCCACCAAAAACTCTT)3' (SEQ ID NO: 15)
5'(GCATCCACCATAAACTCTT)3' (SEQ ID NO: 17)
5'(GCATCCACCAAATACTCTT)3' (SEQ ID NO: 16)
5'(GCATCCACCATATACTCTT)3' (SEQ ID NO: 18)
"Single sequence" primer M34
5'(CCACTGTGTGCCCTTTGTTCCT)3' (SEQ NO: 25)

In a preferred embodiment, the relative molar ratios of individual oligonucleotide components of F2, R2, and M34 were 0.25:0.125:1, respectively. It will be evident to those skilled in the art that other molar ratios of the oligonucleotide primers, particularly ratios that increase the relative amount of the primers present in lowest concentration, may be advantageous.

Finally, 1 µl of template DNA from the first stage PCR product was added. The total reaction volume was 50 µl. The PCR reaction was carried out in the Perkin-Elmer thermal cycler for 30 cycles as in the first stage PCR.

Nested PCR is an extremely sensitive method for amplification of DNA. An amount of $10^{12}$ DNA copies can be generated from one template sequence.

Depending on the type of thermal cycler used, it may be necessary to overlay each tube with 2 drops of mineral oil (40–60 µl) to prevent formation of condensation. In this case it is recommended to overlay mineral oil before adding the samples into the tubes as set forth above.

Interpretation and Analysis of PCR Results

PCR products are analyzed by using standard gel electrophoresis. An amount of 10 µl of amplified DNA from the second stage PCR was run on 1.0 to 1.4% agarose or 2–3% metaphor agarose.

Figure 2:
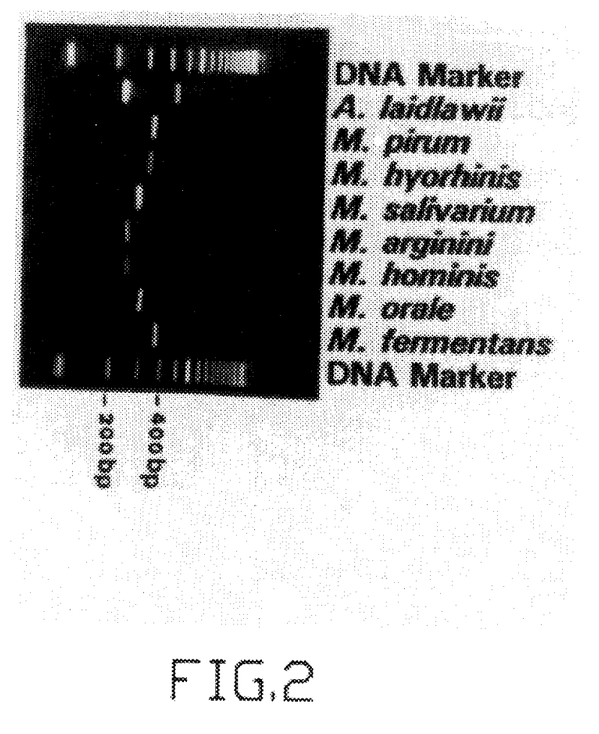
FIG. 2 is an agarose gel showing the relative sizes of the amplicon bands produced following amplification of Mycoplasma and Acholeplasma DNA.

Identification can be done using size identification method or using known restriction digest mapping in order to identify the specific mycoplasma species present in a sample. For example, the size of each second stage PCR amplicon can be estimated by resolving the product in 1.2–1.4% agarose, 3–4% Nusieve 3:1 agarose, 2–3% metaphore agarose gel, or using 5% polyacrylamide gel electrophoresis followed by ethidium bromide staining and observation. The migration pattern of the amplicons from the eight commonly encountered mycoplasma species is shown in FIG. 2.

In addition, restriction endonucleases (i.e., VspI, ClaI, HindIII) can be used to digest the second stage PCR products from the commonly encountered mycoplasma. The sizes of the restriction digest fragments for each Mycoplasma species are presented in Table 2.

TABLE 2

Variations of restriction fragment lengths of the 16S–23S rRNA intergenic spacer regions of commonly encountered species of mycoplasma.

| Mycoplasma Species | Second Stage PCR Product | Restriction Fragments | | |
|---|---|---|---|---|
| | | Vsp I | Hind III | Cla I |
| M. arginini | 236 bp | 134, 102 | —* | — |
| M. fermentans | 365 | 270, 95 | 241, 124 | — |
| M. hominis | 236** | 123, 113 | — | — |
| M. hyorhinis | 315 | — | — | 253, 62 |
| M. orale | 290 | 151, 139 | — | — |
| M. pirum | 323 | 169, 154 | 285, 38 | — |
| M. salivarium | 269 | — | — | — |
| A. laidlawii | 426, 219 | 219, 198, 189, 39 | — | — |

* "—" means no restriction site observed.
**When polyacrylamide gel is used for the resolution of amplified DNA products, a double band product with one base pair difference may be observed for M. hominis. This feature can serve as a good indicator for differentiating M. hominis from M. arginini, which only produces a single band DNA product.

The above results demonstrate that the present invention detects seven commonly encountered Mycoplasma contaminants of cell cultures plus A. laidlawii.

Example 2

In order to determine the sensitivity of the present detection system the following experiment was performed. Serial dilution of actively growing Mycoplasma and Acholeplasma cultures was done, and the diluted aliquots were plated on appropriate media to obtain 30–300 colonies per plate. The diluted aliquots were then subjected directly to nested PCR amplification as outlined above. After the colony counts were obtained, the total number of colony forming units (CFU) present in the diluted aliquots subjected to nested PCR amplification was calculated. The total CFU counts were correlated with the PCR results, and the sensitivity of detection was determined. The results of the sensitivity testing are shown in Table 3.

TABLE 3

Sensitivity Testing of Example 1 Species

| NAME | ATCC # | SENSITIVITY |
|---|---|---|
| A. laidlawii | 23206 | 20 CFU/ml (0.1 cell/5 µl) |
| M. fermentans | 19989 | 100 CFU/ml (0.5 cell/5 µl) |
| M. pirum | 25960 | 100 CFU/ml (0.5 cell/5 µl) |
| M. hyorhinis | 17981 | 100 CFU/ml (0.5 cell/5 µl) |
| M. orale | 23714 | 320 CFU/ml (1.6 cell/5 µl) |
| M. hominis | 23114 | 100 CFU/ml (0.5 cell/5 µl) |
| M. salivarium | 23064 | 180 CFU/ml (0.9 cell/5 µl) |

The above results demonstrate the enhanced sensitivity of the present invention. Specifically, as low as 20 CFU/ml could be detected for A. laidlawii. The sensitivity of A. laidlawii from other known mycoplasma detection systems is around 1000 CFU/ml (Harasawa et al. (1993) at 227–231). For other Mycoplasma species, the present invention can detect less than one CFU per 5 µl sample, or less than 200 CFU/ml (except for M. orale). Other known mycoplasma detection systems report the detection of one cell per sample, or 1000 CFU/ml.

Example 3

To illustrate the increased sensitivity of detection of A. laidlawii DNA by the combination of primers shown in Table 1 compared to the oligonucleotide primers developed by Harasawa et al, the following experiment was performed. One ng of partially purified (see Example 1) A. laidlawii DNA, and further dilutions of this solution were used as DNA template in the "nested" two stage PCR reaction. Two sets of primer mixtures were compared. One consisted of the primers recommended by Harasawa, et al., i.e. F1 and R1 for the first stage PCR reaction, and F2 and R2 for the second stage PCR reaction. The other consisted of the present first stage primer mixture and the second stage primer mixture of the instant invention, which comprises single sequence primers, along with mixed sequence primers as described in Table 1 above. The primers and A. laidlawii DNA were combined and subjected to "nested" two stage PCR as described in Example 1. The results are summarized in FIG. 3 herein.

Figure 3:
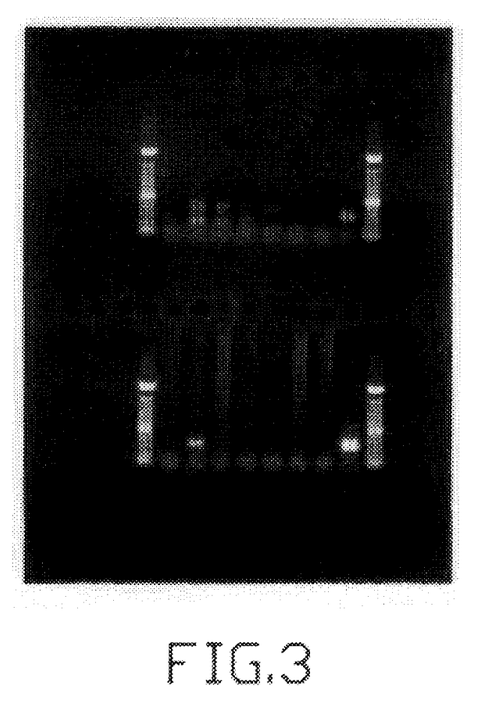
FIG. 3 is an agarose gel showing the relative sizes of amplicon bands produced following amplification of *A. laidlawii* DNA using Harasawa primers and primers of the present invention.

Note that no typical two band A. laidlawii amplicon pattern is seen with the Harasawa primers, even with a concentrated amount of 1 ng of A. laidlawii DNA present as template in the reaction. In contrast, the primer mixtures of the instant invention are able to produce the typical two band A. laidlawii amplicon pattern even at a 1:1000 dilution of the 1 ng of A. laidlawii DNA template. This demonstrates the enhanced sensitivity of detection of A. laidlawii using the primer mixtures described herein, wherein a mixture of mixed sequence primers and single sequence primers are used, as compared to use of only mixed sequence primers as described by Harasawa et al.

Example 4

The following single sequence primers were combined with only the second stage "mixed sequence" primer F2 (see Table 1) and tested for the ability to amplify DNA from a variety of sources using the second stage reaction conditions described above.

R32: [5'(TATATTGGTGGAGCCTAGCGG)3' (SEQ ID NO: 26)]

R33: [5'(ATTGGTGGAGCCTAGCGG)3' (SEQ ID NO: 27)]

M34: [5'(CCACTGTGTGCCCTTTGTTCCT)3' (SEQ ID NO: 25)]

The results are summarized in Table 4 below.

TABLE 4

Comparison of different possible "single sequence" A. laidlawii primers for only the 2nd stage amplification reaction

| Sample | Primers F2 + R32 | Primers F2 + R33 | Primers F2 + M34 |
|---|---|---|---|
| A. laidlawii (ATCC 23206) | Single band | Single band | T (Doub. band) |
| A. laidlawii (ATCC 31166) | Single band | Single band | T (Doub. band) |
| M arginini (ATCC 23838) | 0 | 0 | 0 |
| M fermentans (ATCC 19989) | 0 | 0 | AT |
| M. hominis (ATCC 23114) | Single band | Single band | 0 |
| M. salivarium (ATCC 23064) | Single band | Single band | 0 |
| M hyorhinis (ATCC 17981) | 0 | 0 | 0 |
| M. orale (ATCC 23714) | 0 | 0 | 0 |
| M pirum (ATCC 25960) | 0 | 0 | 0 |
| Bacillus subtilis (ATCC 6051) | T | 0 | 0 |
| Lactobacillus rhamnosus (ATCC 7469) | AT | AT | Single band |
| L. casei (ATCC 393) | 0 | AT | Single band |
| Enterococcus faecalis | 0 | 0 | 0 |

TABLE 4-continued

Comparison of different possible "single sequence" A. laidlawii primers for only the 2nd stage amplification reaction

| Sample | Primers F2 + R32 | Primers F2 + R33 | Primers F2 + M34 |
|---|---|---|---|
| (ATCC 19433) | | | |
| Escherichia coli (ATCC 11775) | 0 | 0 | 0 |
| Clostridium ramosum (ATCC 25582) | 0 | 0 | 0 |
| Clostridium innocuum (ATCC 14501) | 0 | 0 | 0 |
| Lactobaciilus catenaformis (ATCC 25536) | 0 | 0 | 0 |
| Clostridium pasteurianum (ATCC 6013) | 0 | 0 | 0 |
| negative control | 0 | 0 | 0 |

T = typical two band (A. laidlawii) or single band (Mycoplasma) DNA amplicon band observed
0 = no amplicon bands seen
AT = amplicon band(s) seen outside the size range of Mycoplasma and Acholeplasma ampiicons Note that when oligonucleotides R32 and R33 were used, amplicon bands that could have confused the interpretation of results with M. hominis, M. salivarium, were observed. A similar, potentially confusing band was noted for B. subtilis. However, this was not the case with M34. Although M34 does show amplification with L. rhamnosus and L. casei, it was selected for further testing as being preferable to R32 or R33.

Example 5

A first stage PCR reaction was performed using a variety of template DNAs and a first stage primer mixture containing F1, M78, R1 and M89 (see Table 1). An aliquot of the first stage reaction product was combined with a second stage primer mixture containing (F2, R2, and R32) or (F2, R2, and M34) and then second stage PCR amplification was carried out. The results are summarized in Table 5 below.

Note that when the second stage primer mixture (F2, R2, and R32) was used, a cross reaction with a variety of mammalian DNA samples and B. subtilis was observed. The second stage primer mixture (F2, R2, and R32) also gave an atypical one band pattern with A. laidlawii. M34 was again considered preferable to R32.

TABLE 5

Comparative specificity of R32 and M34 with a variety of DNA templates.

| Sample | Primer mixture (F2, R2, R32) | Primer mixture (F2, R2, M34) |
|---|---|---|
| mouse DNA (ATCC HB 144) | AT | 0 |
| mouse DNA (ATCC HB 96) | AT | 0 |
| mouse DNA (ATCC HB 72) | AT | 0 |
| mouse DNA (ATCC HB 167) | AT | 0 |
| rat DNA (ATCC HB 221) | AT | 0 |
| rat DNA (ATCC HB 219) | AT | 0 |
| hamster DNA (ATCC HB 226) | AT | 0 |
| human DNA (ATCC CRL 1611) | 0 | 0 |
| human DNA (ATCC CCL 119) | 0 | 0 |
| human DNA (ATCC HTB 31) | 0 | 0 |
| human DNA (ATCC CCL 187) | 0 | 0 |
| monkey DNA (ATCC CCL 81) | AT | S |
| monkey DNA (ATCC CRL 1587) | AT | S |
| rat DNA (ATCC HB 229) | AT | S |
| hamster DNA (ATCC HB 218) | AT | S |
| mouse DNA (ATCC HB 194) | AT | S |
| human DNA (ATCC CCL 86) | AT | S |
| Bacilius subtilis (ATCC 6051) | Single band | 0 |
| Lactobacilius (L.) rhamnosus (ATCC 7469) | 0 | Single band |
| L. casei (ATCC 393) | 0 | Single band |
| M. hominis (ATCC 23114) | Single band | T |
| A. laidlawii (ATCC 23206) | Single band | T (Double band) |
| negative control | 0 | 0 |

T = typical one-band (Mycopiasma) or two-band (Acholeplasma) amplicon pattern observed
0 = no amplicon bands observed
AT = multiple amplicon bands observed, outside size range of typical one or two band pattern
S = smear without identiflabie specific amplicon bands

Example 6

A first stage PCR reaction was performed using a variety of template DNAs and the first stage primer mixture containing F1, M78, R1 and M89 (see Table 1). An aliquot of the first stage reaction product was combined with either the primer mixture (F2, R2, R32) or (F2, R2, M34) and second stage PCR amplification was carried out. The results are summarized in Table 6.

TABLE 6

Comparative specificity of "single sequence" primers R32 and M34 with Mycoplasma DNA templates

| Sample | Primer mixture (F2, R2, R32) | Primer mixture (F2, R2, M34) |
|---|---|---|
| Acholeplasma laidlawii (ATCC 23206) | atypical one band pattern | typical two band pattern |
| Mycoplasma fermentans | T | T |
| M. hyorhinis | T | T |
| M. pirum | T | T |
| M. hominis | T | T |
| M. arginini | T | T |
| M. roale | T | T |
| M. salivarium | T | T |
| negative control | 0 | 0 |

T = typical one-band (Mycoplasma) or two-band (Acholeplasma) amplicon pattern observed
0 = no amplicon bands observed The atypical one band pattern observed when primer R32 was used in place of M34 again favors the use of M34.

All references cited herein are incorporated herein in their entirety. It will be evident that obvious modifications and applications can be made to the teachings herein without departing from the spirit and the scope of the instant invention.

We claim:

1. A method for amplifying a target segment of nucleic acid of Mollicutes in a sample nucleic acid mixture by performing a two stage polymerase chain reaction to selectively amplify a nucleic acid comprising said target segment of nucleic acid of said sample nucleic acid mixture, wherein said method comprises the steps of:

adding a first stage PCR primer set for amplifying a target segment of nucleic acid to a sample nucleic acid mixture to amplify nucleic acid sequences flanked by primers in said first stage PCR primer set and containing said target segment, wherein said first stage PCR primer set comprises single sequence primers complementary to said nucleic acid sequences including 5'(AAAGTGGGCAATACCCAACGC)3' (SEQ ID NO: 23), and 5'(TCACGCTTAGATGCTTTCAGCG)3' (SEQ ID NO: 24), and at least one of a first mixed sequence primer set including primers complementary to said nucleic acid sequences selected from the group consisting of 5'(ACACCATGGGAGCTGGTAAT)3' (SEQ ID NO: 1), and 5'(ACACCATGGGAGTTGGTAAT)3' (SEQ ID NO: 2), and at least one of a second mixed sequence primer set including primers complementary to said nucleic acid selected from the group consisting of

5'(CTTCATCGACTTCGAGACCCAAGGCAT)3' (SEQ ID NO. 19),

5'(CTTCTTCGACTTTCAGACCCAAGGCAT)3' (SEQ ID NO. 22),

5'(CTTCATCGACTTTCAGACCCAAGGCAT)3' (SEQ ID NO. 21), and

5'(CTTCTTCGACTTCCAGACCCAAGGCAT)3' (SEQ ID NO. 20) wherein said primers hybridize to Mollicutes nucleic acids;

adding a second stage PCR primer set for amplifying said target segment of nucleic acid to said sample nucleic acid mixture to amplify nucleic acid sequences flanked by primers in said second stage PCR primer set and containing said target segment, wherein said second stage PCR primer set comprises a single sequence primer complementary to said nucleic acid sequences having the sequence 5'(CCACTGTGTGCCCTTTGTTCCT)3' (SEQ ID NO: 25), and at least one of a first mixed sequence primer set including primers complementary to said nucleic acid sequences selected from the group consisting of

5'(GTGCGGATGGATCACCTCCT)3' (SEQ ID NO: 7),

5'(GTGGGGCTGGATCACCTCCT)3' (SEQ ID NO: 10),

5'(GTGCGGCTGGATCACCTCCT)3' (SEQ ID NO: 9), and

5'(GTGGGGATGGATCACCTCCT)3' (SEQ ID NO: 8), and at least one of a second mixed sequence primer set including primers complementary to said nucleic acid sequences selected from the group consisting of

5'(GCATCCACCAAAAACCCTT)3' (SEQ ID NO: 11),

5'(GCATCCACCAAAAACTCTT)3' (SEQ ID NO: 15),
5'(GCATCCACCAAATACCCTT)3' (SEQ ID NO: 13),
5'(GCATCCACCAAATACTCTT)3' (SEQ ID NO: 16),
5'(GCATCCACCATAAACCTT)3' (SEQ ID NO: 12),
5'(GCATCCACCATAAACTCTT)3' (SEQ ID NO: 17),
5'(GCATCCACCATATACCCTT)3' (SEQ ID NO: 14), and
5'(GCATCCACCATATACTCTT)3' (SEQ ID NO: 18) wherein said primers hybridize to Mollicutes nucleic acids; and repetitively performing polymerase chain reaction after both of said adding steps.

2. The method of claim 1 further comprising the step of selecting the target segment of nucleic acid to be comprised of deoxyribonucleic acid.

3. The method of claim 2 further comprising the step of selecting the target segment of nucleic acid to be diagnostic of a selected Mollicutes.

4. The method of claim 3 further comprising the step of selecting the sample nucleic acid mixture to be comprised of deoxyribonucleic acid extracted from biological samples of undetermined identity.

5. The method of claim 1 further comprising the step of detecting the presence of the amplified target segment.

6. The method of claim 5 further comprising the step of identifying a particular genus, species or subspecies of Mollicutes in the nucleic acid mixture.

7. The method of claim 1, wherein the particular genus of Mollicutes is Mycoplasma or Acholeplasma.

8. The method of claim 7, wherein the particular species is selected from the group consisting of *Acholeplasma laidlawii, Mycoplasma fermentans, Mycoplasma hyorhinis, Mycoplasma orale, Mycoplasma arginini, Mycoplasma pirum, Mycoplasma hominis,* and *Mycoplasma salivarium.*

9. The method of claim 8, wherein the particular species is *A. laidlawii.*

10. A Mollicutes test kit for detection of the presence of an amplified target segment of a nucleic acid in a nucleic acid mixture by use of two stage polymerase chain reaction, comprising:

a first vessel containing a first stage PCR primer set which comprises single sequence primers complementary to said nucleic acid including 5'(AAAGTGGGCAATACCCAACGC)3' (SEQ ID NO: 23), and 5'(TCACGCTTAGATGCTTTCAGCG)3' (SEQ ID NO: 24), and at least one of a first mixed sequence primer set including primers complementary to said nucleic acid selected from the group consisting of 5'(ACACCATGGGAGCTGGTAAT)3' (SEQ ID NO: 1), and 5'(ACACCATGGGAGTTGTAAT)3' (SEQ ID NO: 2), and at least one of a second mixed sequence primer set including primers complementary to said nucleic acid selected from the group consisting of

5'(CTTCATCGACTTCCAGACCCAAGGCAT)3' (SEQ ID NO. 19),

5'(CTTCTTCGACTTTCAGACCCAAGGCAT)3' (SEQ ID NO. 22),

5'(CTTCATCGACTTTCAGACCCAAGGCAT)3' (SEQ ID NO. 21), and

5'(CTTCTTCGACTTCCAGACCCAAGGCAT)3' (SEQ ID NO. 20) wherein said primers hybridize to Mollicutes nucleic acids;

a second vessel containing a second stage PCR primer set which comprises a single sequence primer complementary to said nucleic acid having the sequence 5'(CCACTGTGTGCCCTTTGTTCCT)3' (SEQ ID NO: 25), and at least one of a first mixed sequence primer set including primers complementary to said nucleic acid selected from the group consisting of

5'(GTGCGGATGGATCACCTCCT)3' (SEQ ID NO: 7),

5'(GTGGGGCTGGATCACCTCCT)3' (SEQ ID NO: 10),

5'(GTGCGGCTGGATCACCTCCT)3' (SEQ ID NO: 9), and

5'(GTGGGGATGATCACCTCCT)3' (SEQ ID NO: 8), and at least one of a second mixed sequence primer set including primers complementary to said nucleic acid selected from the group consisting of 5'(GCATCCACCAAAAACCCTT)3' (SEQ ID NO: 11),
5'(GCATCCACCAAAAACTCTT)3' (SEQ ID NO: 15),
5'(GCATCCACCAAATACCCTT)3' (SEQ ID NO: 13),
5'(GCATCCACCAAATACTCTT)3' (SEQ ID NO: 16),
5'(GCATCCACCATAAACCTT)3' (SEQ ID NO: 12),
5'(GCATCCACCATAAACTCTT)3' (SEQ ID NO: 17),
5'(GCATCCACCATATACCCTT)3' (SEQ ID NO: 14), and
5'(GCATCCACCATATACTCTT)3' (SEQ ID NO: 18) wherein said primers hybridize to Mollicutes nucleic acids;

a third vessel containing a first positive control nucleic acid; and a fourth vessel containing a second positive control nucleic acid.

11. The kit of claim 10 wherein said primers in said first and second stage PCR primer sets immediately flank a DNA segment diagnostic of a particular class, genus, species or subspecies of microorganisms.

12. The kit of claim 10, wherein the particular genus of Mollicutes is Mycoplasma or Acholeplasma.

13. The kit of claim 12, wherein the particular species is selected from the group consisting of *Acholeplasma laidlawii, Mycoplasma fermentans, Mycoplasma hyorhinis, Mycoplasma orale, Mycoplasma arginini, Mycoplasma pirum, Mycoplasma hominis,* and *Mycoplasma salivarium.*

14. The kit of claim 13 wherein the particular species is *Acholeplasma laidlawii.*

15. A first stage PCR primer set for amplifying a target segment of nucleic acid of Mollicutes in a sample nucleic acid mixture which comprises:

single sequence primers complementary to said nucleic acid including

5'(AAAGTGGGCAATACCCAACGC)3' (SEQ ID NO: 23), and

5'(TCACGCTTAGATGCTTTCAGCG)3' (SEQ ID NO: 24); and at least one of a first mixed sequence primer set including primers complementary to said nucleic acid selected from the group consisting of 5'(ACACCATGGGAGCTGGTAAT)3' (SEQ ID NO: 1), and 5'(ACACCATGGGAGTTGGTAAT)3' (SEQ ID NO: 2); and at least one of a second mixed sequence primer set including primers complementary to said nucleic acid selected from the group consisting of

5'(CTTCATCGACTTCCAGACCCAAGGCAT)3' (SEQ ID NO: 19),

5'(CTTCTTCGACTTTCAGACCCAAGGCAT)3' (SEQ ID NO: 22),

5'(CTTCATCGACTTTCAGACCCAAGGCAT)3' (SEQ ID NO: 21), and

5'(CTTCTTCGACTTCCAGACCCAAGGCAT)3' (SEQ ID NO: 20) wherein said primers hybridize with Mollicutes nucleic acids.

16. A second stage PCR primer set for amplifying a target segment of nucleic acid of Mollicutes in a sample nucleic acid mixture which comprises:

a single sequence primer complementary to said nucleic acid having the sequence

5'(CCACTGTGTGCCCTTTGTTCCT)3' (SEQ ID NO: 25); and at least one of a first mixed sequence primer set including primers complementary to said nucleic acid selected from the group consisting of 5'(GTGCGGATGGATCACCTCCT)3' (SEQ ID NO: 7),
5'(GTGGGGCTGGATCACCTCCT)3' (SEQ ID NO: 10),
5'(GTGCGGCTGGATCACCTCCT)3' (SEQ ID NO: 9), and
5'(GTGGGGATGGATCACCTCCT)3' (SEQ ID NO: 8); and at least one of a second mixed sequence primer set including primers complementary to said nucleic acid selected from the group consisting of 5'(GCATCCACCAAAAACCCTT)3' (SEQ ID NO: 11),
5'(GCATCCACCAAAAACTCTT)3' (SEQ ID NO: 15),
5'(GCATCCACCAAATACCCTT)3' (SEQ ID NO: 13),
5'(GCATCCACCAAATACTCTT)3' (SEQ ID NO: 16),
5'(GCATCCACCATAAACCCTT)3' (SEQ ID NO: 12),
5'(GCATCCACCATAAACTCTT)3' (SEQ ID NO: 17), 5'(GCATCCACCATATACCCTT)3' (SEQ ID NO: 14), and 5'(GCATCCACCATATACTCTT)3' (SEQ ID NO: 18) wherein said primers hybridize to Mollicutes nucleic acids.

17. The first stage PCR primer set of claim 15, comprising:

5'(ACACCATGGGAGCTGGTAAT)3' (SEQ ID NO: 1),
5'(ACACCATGGGAGTTGGTAAT)3' (SEQ ID NO: 2),
5'(AAAGTGGGCAATACCCAACGC)3' (SEQ ID NO: 23),
5'(CTTCATCGACTTCCAGACCCAAGGCAT)3' (SEQ ID NO: 19),
5'(CTTCTTCGACTTTCAGACCCAAGGCAT)3' (SEQ ID NO: 22),
5'(CTTCATCGACTTTCAGACCCAAGGCAT)3' (SEQ ID NO: 21),
5'(CTTCTTCGACTTCCAGACCCAAGGCAT)3' (SEQ ID NO: 20), and
5'(TCACGCTTAGATGCTTTCAGCG)3' (SEQ ID NO: 24).

18. The second stage PCR primer set of claim 16, comprising:

5'(GTGCGGATGGATCACCTCCT)3' (SEQ ID NO: 7),
5'(GTGGGGCTGGATCACCTCCT)3' (SEQ ID NO: 10),
5'(GTGCGGCTGGATCACCTCCT)3' (SEQ ID NO: 9),
5'(GTGGGGATGGATCACCTCCT)3' (SEQ ID NO: 8),
5'(GCATCCACCAAAAACCCTT)3' (SEQ ID NO: 11),
5'(GCATCCACCAAAAACTCTT)3' (SEQ ID NO: 15),
5'(GCATCCACCAAATACCCTT)3' (SEQ ID NO: 13),
5'(GCATCCACCAAATACTCTT)3' (SEQ ID NO: 16),
5'(GCATCCACCATAAACCCTT)3' (SEQ ID NO: 12),
5'(GCATCCACCATAAACTCTT)3' (SEQ ID NO: 17),
5'(GCATCCACCATATACCCTT)3' (SEQ ID NO: 14),
5'(GCATCCACCATATACTCTT)3' (SEQ ID NO: 18), and
5'(CCACTGTGTGCCCTTTGTTCCT)3' (SEQ ID NO: 25).

* * * * *